United States Patent [19]

Mirviss

[11] Patent Number: 4,767,884

[45] Date of Patent: Aug. 30, 1988

[54] REDUCTION OF SULFONIC ACID TO THIOL

[75] Inventor: Stanley B. Mirviss, Stamford, Conn.

[73] Assignee: Akzo America Inc., New York, N.Y.

[21] Appl. No.: 97,881

[22] Filed: Sep. 17, 1987

[51] Int. Cl.$^4$ ............................................. C07C 148/00
[52] U.S. Cl. .......................................... 568/68; 568/69
[58] Field of Search ....................... 568/58, 59, 60, 67, 568/68, 69

[56] References Cited

FOREIGN PATENT DOCUMENTS 7062252 4/1982 Japan ...................................... 568/67
85/5354 12/1985 World Int. Prop. O. ............. 568/67

OTHER PUBLICATIONS

Kirk–Othmer Encyclopedia of Chemical Technology, Third Edition, vol. 18, pp. 265 and 275 (1982); Supplement volume pp. 19 and 41 (1984).

J. March, Advanced Organic Chemistry, Third Edition, p. 1076 (1985).

L. Numata et al, Tetrahedron Letters, vol. 21, pp. 1235–1238 (1980).

*Primary Examiner*—Mary E. Ceperley
*Attorney, Agent, or Firm*—Richard P. Fennelly; Francis W. Young; Louis A. Morris

[57] ABSTRACT

A sulfonic acid is reduced to a thiol by heating the acid under carbon monoxide pressure in the presence of a rhodium carbonyl catalyst.

8 Claims, No Drawings

REDUCTION OF SULFONIC ACID TO THIOL

BACKGROUND OF THE INVENTION

1. Field of the Invention

The present invention relates to the reduction of a sulfonic acid to its corresponding thiol.

2. Description of the Prior Art

Sulfonic acids, e.g., such aryl sulfonic acids as benzenesulfonic acid, are described as being directly reducible to the corresponding thiols by use of a trifluoroacetic anhydride-tetrabutylammonium iodide mixture by T. Numata et al. in Tetrahedron Letters, Vol. 21, 1235-1238 (1980). This route is indicated as being the "first example" of the direct reduction of such sulfonic acids to the corresponding thiol. Numata et al. do indicate, however, that various sulfonic acid derivatives (e.g., the sulfonyl halide, sulfonamide, and sulfonate derivatives) are reducible with more typical reducing agents.

SUMMARY OF THE PRESENT INVENTION

It has now been found possible to reduce a sulfonic acid to its corresponding thiol by using a rhodium carbonyl catalyst under heat and carbon monoxide pressure.

DETAILED DESCRIPTION OF THE INVENTION

The present invention relates to the reduction of a known class of compounds (the sulfonic acids) to their corresponding thiols. The starting acids are of the formula $ArSO_3H$ with Ar representing a substituted or unsubstituted benzene ring. An example is benzenesulfonic acid. The corresponding thiols have the formula ArSH with thiophenol (a known chemical intermediate) being a representative compound.

The conversion of the sulfonic acid to the thiol can be achieved under conditions of superatmospheric pressure (e.g., about 500 to about 5000 psi) and elevated temperature (e.g., about 125° C. to about 350° C.) using a catalytically effective amount (e.g., from about 0.1% to about 10%, based on the weight of sulfonic acid) of a rhodium carbonyl. Representative rhodium carbonyls include $Rh_4(CO)_{12}$, $Rh_6(CO)_{16}$, and $Rh_2(CO)_8$. Preferred reaction conditions are 750-3000 psi and 150°-300° C.

The present invention is further illustrated by the Examples which follow.

EXAMPLE 1

A 300-milliliter 316-stainless steel autoclave was charged with 25 grams of benzenesulfonic acid (90% pure), 100 milliliters (88 grams) of benzene and 0.3 gram of hexarhodium hexadecacarbonyl, $Rh_6(CO)_{16}$, catalyst (1.2 wt. % based on benzenesulfonic acid). The autoclave was pressured with carbon monoxide to 1500 psig and was heated for 10 hours at 180° C. The maximum carbon monoxide pressure developed at 180° C. was 2400 psig. The autoclave was then cooled to room temperature.

Gas chromatographic analysis of the reactor contents showed that thiophenol was formed in approximately 35-40% yield with essentially no by-products.

EXAMPLE 2

The procedure was the same as Example 1 with the exception that 0.8 gram of catalyst (3.2 wt. % on benzenesulfonic acid) was employed and the reaction was run for 10 hours at 250° C. The yield of thiophenol was about 15-20% and small yields of diphenyl sulfide (2%) and diphenyl sulfone (8%) were formed.

COMPARATIVE EXAMPLES 3-5

When Examples 1 or 2 were run with and without triphenyl phosphine promoter with 0.5 gram of cobalt carbonyl, no thiophenol was formed. Similar results were obtained with chromium carbonyl and with iron pentacarbonyl under the conditions of Example 2.

COMPARATIVE EXAMPLE 6

When Example 2 was run without catalyst, only traces of thiophenol, diphenyl sulfide, and diphenyl sulfone were formed. Analysis showed traces of nickel and chromium in the liquid.

COMPARATIVE EXAMPLE 7

Example 2 was repeated without catalyst and carbon monoxide. No thiophenol or diphenyl sulfide were formed. A small amount (3%) of diphenyl sulfone was present.

COMPARATIVE EXAMPLE 8

Use of the sodium salt of benzenesulfonic acid and iron pentacarbonyl using the reaction conditions of Examples 1 and 2, with and without extra sodium hydroxide, gave no thiophenol but did produce a small amount (2-3%) of diphenyl sulfone.

The foregoing should merely be considered to be exemplary of the instant invention and should not therefore be considered in a limiting sense. The scope of protection that is sought is set forth in the claims which follow.

I claim:

1. A process for the reduction of a sulfonic acid to a thiol which comprises heating the sulfonic acid, under pressure, at elevated temperature in the presence of carbon monoxide and a catalytically effective amount of a rhodium carbonyl to form the thiol.

2. A process as claimed in claim 1 wherein the rhodium carbonyl catalyst is $Rh_6(CO)_{16}$.

3. A process as claimed in claim 1 wherein the sulfonic acid is benzenesulfonic acid.

4. A process as claimed in claim 2 wherein the sulfonic acid is benzenesulfonic acid.

5. A process as claimed in claim 1 wherein the pressure ranges from about 500 to 5000 psi and the temperature from about 125° C. to about 350° C.

6. A process as claimed in claim 1 wherein the amount of catalyst ranges from about 0.1% to about 10%, by weight of the sulfonic acid.

7. A process as claimed in claim 1 wherein the sulfonic acid is benzenesulfonic acid and the catalyst is $Rh_6(CO)_{16}$ at from about 0.1% to 10% by weight of the sulfonic acid.

8. A process as claimed in claim 7 wherein the pressure is from about 750 to about 3000 psi and the temperature is from about 150° C. to about 300° C.

* * * * *